(12) United States Patent
Shepard et al.

(10) Patent No.: US 6,668,039 B2
(45) Date of Patent: Dec. 23, 2003

(54) COMPACT X-RAY FLUORESCENCE SPECTROMETER AND METHOD FOR FLUID ANALYSIS

(75) Inventors: Chester L. Shepard, West Richland, WA (US); Bary W. Wilson, Richland, WA (US); Leslie J. Kirihara, Richland, WA (US); John T. Munley, Benton City, WA (US); James H. Reeves, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1 day.

(21) Appl. No.: 10/041,331

(22) Filed: Jan. 7, 2002

(65) Prior Publication Data

US 2003/0128805 A1 Jul. 10, 2003

(51) Int. Cl.[7] ............................................. G01N 23/223
(52) U.S. Cl. .............................. 378/47; 378/44; 378/45
(58) Field of Search ............................... 378/44, 45, 47

(56) References Cited

U.S. PATENT DOCUMENTS

| | | | |
|---|---|---|---|
| 3,751,661 A | 8/1973 | Packer et al. ................. 378/47 |
| 3,889,125 A | 6/1975 | Gerber | |
| 4,125,769 A | 11/1978 | Marten et al. ................ 378/47 |
| 4,388,530 A | * 6/1983 | Lubecki et al. ............... 378/45 |
| 4,450,576 A | * 5/1984 | Lubecki et al. ............... 378/47 |
| 4,683,759 A | 8/1987 | Skarsvaag et al. | |
| 4,720,842 A | 1/1988 | Kira et al. .................... 378/49 |
| 4,795,903 A | 1/1989 | Clayton | |
| 4,821,301 A | * 4/1989 | Cocks et al. .................. 378/70 |
| 4,916,719 A | 4/1990 | Kawatra et al. | |
| 5,497,008 A | 3/1996 | Kumakhov .............. 250/505.1 |
| 5,598,451 A | 1/1997 | Ohno et al. ................... 378/44 |
| 5,657,363 A | 8/1997 | Hossain et al. | |
| 5,712,891 A | 1/1998 | Benony et al. ............... 378/47 |
| 5,721,759 A | 2/1998 | Raatikainen ................. 378/47 |
| 5,982,847 A | 11/1999 | Nelson ......................... 378/47 |
| 6,012,325 A | 1/2000 | Ma ........................... 73/24.02 |
| 6,226,347 B1 | 5/2001 | Golenhofen | |
| 6,285,734 B1 | 9/2001 | Von Alfthan | |
| 6,408,048 B2 | 6/2002 | Opsal et al. | |

* cited by examiner

Primary Examiner—Edward J. Glick
Assistant Examiner—Allen C. Ho
(74) Attorney, Agent, or Firm—Woodard, Emhardt, Moriarty, McNett & Henry LLP (57) ABSTRACT

An X-ray fluorescence device and method are disclosed. The device includes a source block containing an X-ray source, a substantially X-ray transparent fluid flow path through the source block and proximate the X-ray source, and an X-ray detector separated from the X-ray source by the source block. First and second openings are provided in the source block between the X-ray source and the flow path and between the flow path and the detector respectively. In operation, source X-rays pass through the first opening and through the flow path. A portion of the source X-rays interact with a fluid in the flow path to create a fluid fluorescence response. The remainder of the source X-rays pass into a noise reduction cavity of the source block. The detector receives the portion of the fluid fluorescence response passing through the second opening and produces an output indicative of the presence and amount of selected components in the fluid.

61 Claims, 8 Drawing Sheets

COMPACT X-RAY FLUORESCENCE SPECTROMETER AND METHOD FOR FLUID ANALYSIS

RELATED APPLICATION DATA

This application is related to application Ser. No. 09/776,109 filed Feb. 1, 2001, now U.S. Pat. No. 6,561,010, and to application Ser. No. 09/447,036 filed Nov. 19, 1999, now abandoned.

FIELD OF THE INVENTION

The present invention relates to an apparatus and method for fluid analysis. Particular embodiments of the present invention relate to systems and techniques for X-ray fluorescence analysis of fluids. Still more particular embodiments are related to on-board X-ray analysis of operating machine fluids for the determination of machine health.

BACKGROUND OF THE INVENTION

It is well known that chemical and physical analysis of a machine fluid can provide information about the condition of the fluid as well as the wear status of the machine in which the fluid is used. Machine fluid analysis is widely used for determination of lubricant condition, lubricant contamination and wear status in engines, drive components and hydraulic systems in fleet or industrial service. For example, lubrication oil analysis is widely used for railroad engines and is conducted by the military on most motorized equipment including aircraft and naval engines and lubricated drive components. In industry, commercial fluid analysis providers offer fluid analysis service for engine and drive train lubricants as well as hydraulic fluids.

However, traditionally, an oil sample has been taken from the lubricant reservoir on the engine being analyzed, with fluid parameters then measured in the laboratory. To avoid inefficiencies and difficulties associated with such batch analysis, it is desirable to develop systems and devices capable of operation on board a machine to provide continuous and real time monitoring of machine fluids.

One type of fluid analysis, X-ray fluorescence analysis, has the potential to be used to quantify trace amounts of materials in machine fluids, provided the X-ray fluorescence meter employed is sufficiently sensitive to the material to be detected. However, for a variety of reasons, current X-ray fluorescence meter designs are not readily applicable for on-board machine fluid analysis.

For example, while not as important for most laboratory scale spectrometer applications, for an on-board machine fluid application, it is advantageous to have a compact spectrometer. However, the sensitivity of a spectrometer is typically compromised by attempts to limit its size because, as the device becomes smaller, components necessarily get closer together, increasing the relative significance of noise. In addition, a smaller device may be more susceptible to breaking or failure from the potentially harsh environment on-board a machine. As a final example, in order to be feasible for dedicated application to individual machines, an X-ray fluorescence meter must be economical to manufacture.

Therefore, a need exists for an X-ray fluorescence spectrometer that is both compact and sensitive so as to be useful in on-board machine fluid analysis. A need also exists for an X-ray fluorescence spectrometer that is capable of meeting the rigors of on-board application yet is economical and efficient to construct.

The present invention addresses one or more of these or other needs and provides, in one embodiment, a novel X-ray fluorescence spectrometer. Another embodiment provides a novel method of performing X-ray fluorescence analysis of fluids. Still other embodiments provide improved systems and techniques useful in on-board machine fluid analysis.

SUMMARY OF THE INVENTION

The invention is set forth in the claims below, and the following is not in any way to limit, define, or otherwise establish the scope of legal protection. In general terms, the present invention relates to X-ray fluorescence analysis of fluids, where one particular application of the invention involves X-ray analysis of machine fluids to thereby provide an indication of engine health.

In one embodiment a novel X-ray fluorescence meter is disclosed including a source block containing an X-ray source, a substantially X-ray transparent fluid flow path through the source block and proximate the X-ray source, and a fluorescence X-ray detector mounted to the source block proximate the flow path and separated from the X-ray source by the source block. The source block includes first and second openings between the X-ray source and the flow path and between the flow path and the detector respectively, and the source block defines a noise reduction cavity having an opening thereto adjacent the flow path and opposite the X-ray source. In operation, source X-rays pass through the first opening and through the flow path. A portion of the source X-rays interact with a fluid in the flow path to create a fluid fluorescence response. The remainder of the source X-rays pass into the noise reduction cavity. The detector receives the portion of the fluid fluorescence response passing through the second opening and produces an output indicative of the presence and amount of selected components in the fluid. In one refinement a substantial portion of the source block is material having elements with an atomic number below the atomic number of the element(s) to be detected. In this and in other refinements, the source block is contained in a rigid outer housing including a pair of fluid couplings coupled to the flow path. In any of the above or in still further refinements one or more layers of X-ray shielding material are placed around the source block and/or between the detector and the source block.

In another embodiment there is described herein a novel X-ray fluorescence spectrometer including a source block containing an X-ray source and having a fluid flow path therethrough proximate the X-ray source. The flow path is substantially transparent to source X-rays and is operable to direct a fluid past the X-ray source for interaction of the fluid with source X-rays to produce a fluid fluorescence response to the source X-rays. The spectrometer includes a detector mounted proximate the flow path for receiving at least a portion of the fluorescence response for quantitatively determining the presence of selected components of the fluid. In any refinement, the source block is formed of material comprising elements having a low atomic number such as magnesium, graphite, aluminum, or plastic. In the above or in a further refinement a rigid outer housing surrounds the source block and includes a pair of fluid couplings connected to the flow path for coupling the flow path to a machine fluid line. In any of the above or in still further refinements, the source block defines a noise reduction cavity separated from the detector by the source block and operable to receive source X-rays passing through the flow path. The noise reduction cavity has an opening thereto adjacent the flow path and opposite the X-ray source such that the flow path is between the cavity opening and the X-ray source. In any of the above or in further refinements, one or more layers of X-ray shielding is provided around the source block and/or between the detector and the source block. In any of the above or in further refinements the detector has a detection face substantially parallel to the flow direction for fluid in the flow path. In any of the above or in still further refinements, the detector, the X-ray source, and the flow path proximate the X-ray source form a plane perpendicular to the fluid flow path through the source block.

In another embodiment, a novel method of performing fluid analysis is provided including providing an X-ray fluorescence meter including a source block containing an X-ray source and having a fluid flow path past the X-ray source, passing fluid through the flow path, passing source X-rays through the flow path and into a noise reduction cavity of the source block, and receiving a fluid fluorescence response to the source X-rays with a detector isolated from source X-rays by the source block. In one refinement, the fluid is machine fluid and is passed through the flow path under pressure of a machine. In this or in other refinements, the detected fluorescence response travels in a direction substantially perpendicular to the bulk fluid flow direction and/or in a direction substantially perpendicular to source X-rays passing through the flow path. In any of the above or in further refinements, the source block in contained in a rigid outer housing having a pair of fluid couplings for coupling the fluid through the flow path.

DETAILED DESCRIPTION OF THE PREFERRED EMBODIMENT

For the purposes of promoting an understanding of the principles of the invention reference will now be made to the embodiments illustrated in the drawings and specific language will be used to describe the same where like reference numerals are used to describe like structures. It will nevertheless be understood that no limitation of the scope of the invention is thereby intended. Any alterations and further modifications in the illustrated embodiments, and any further applications of the principles of the invention as illustrated herein being contemplated as would normally occur to one skilled in the art to which the invention relates.

Figure 1:
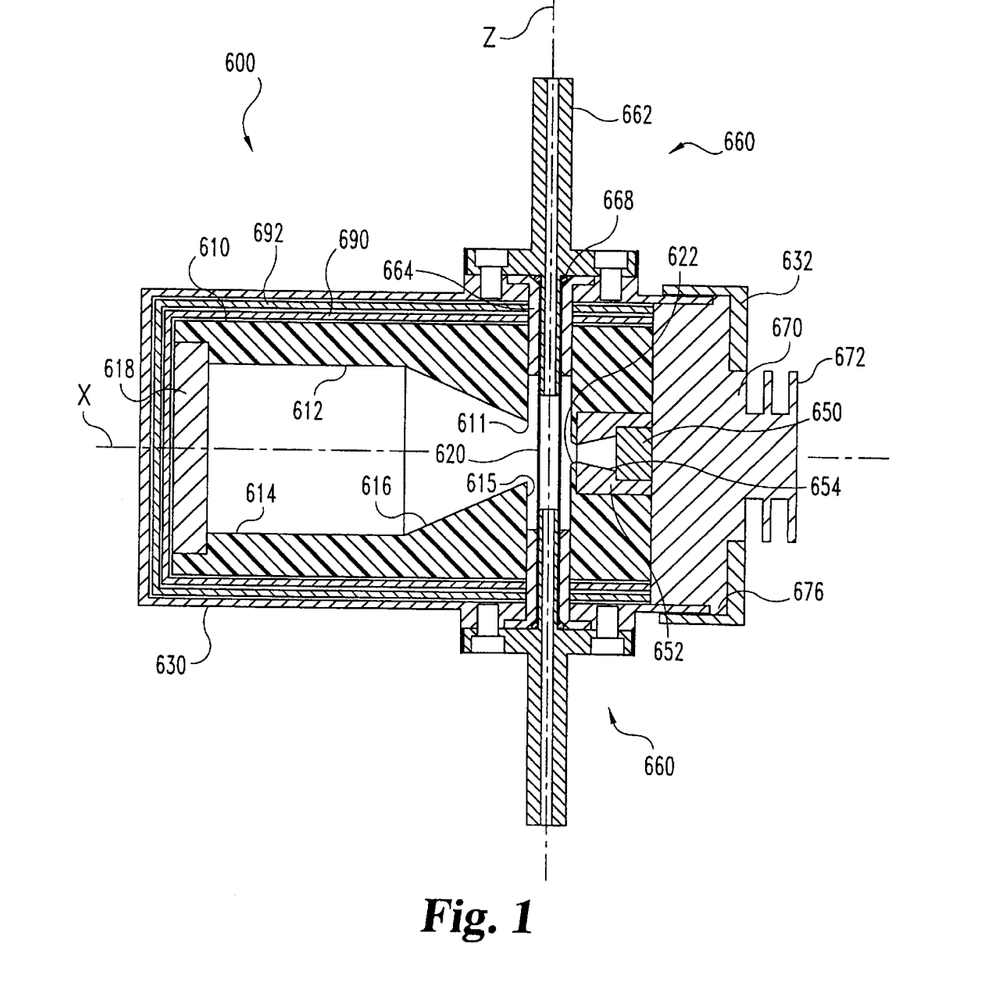
FIG. 1 is a side sectional view of an x-ray fluorescence meter.
Figure 2:
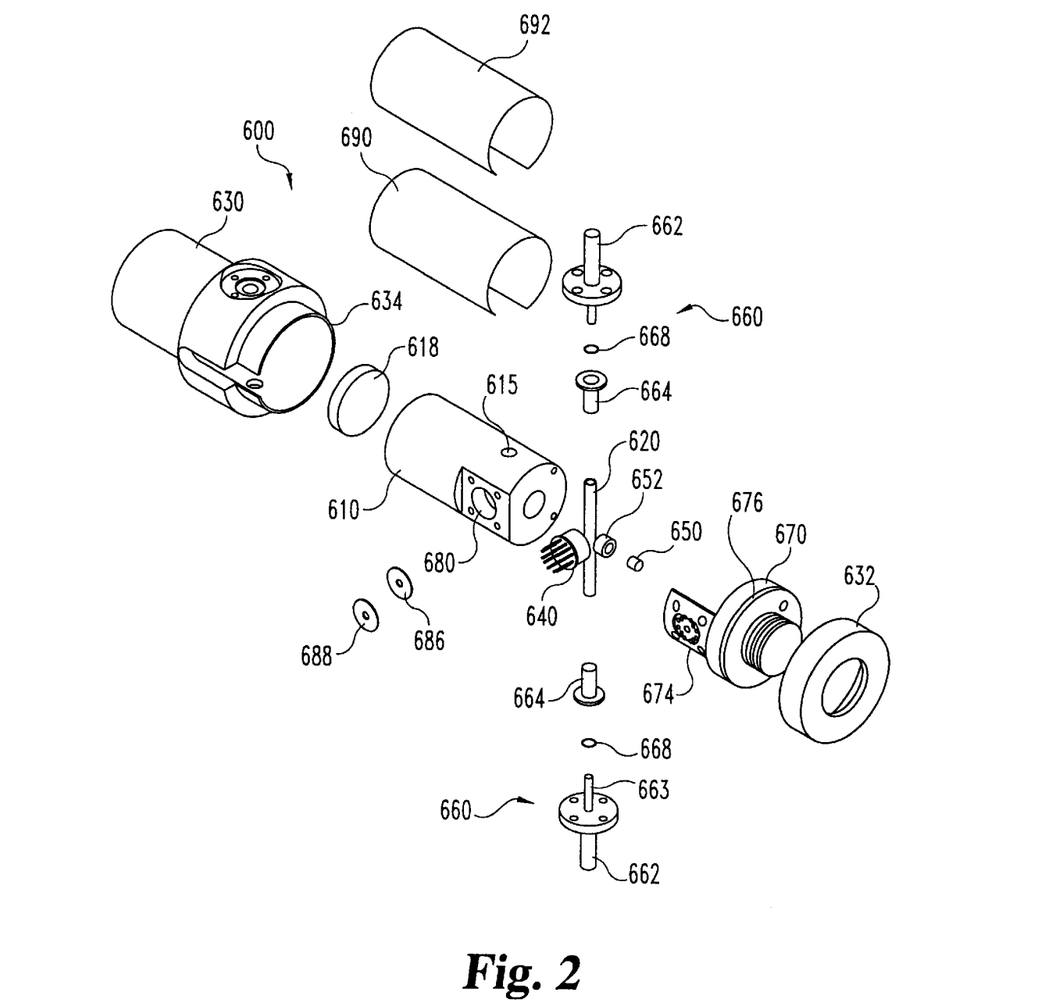
FIG. 2 is an exploded view of the FIG. 1 meter.
Figure 3:
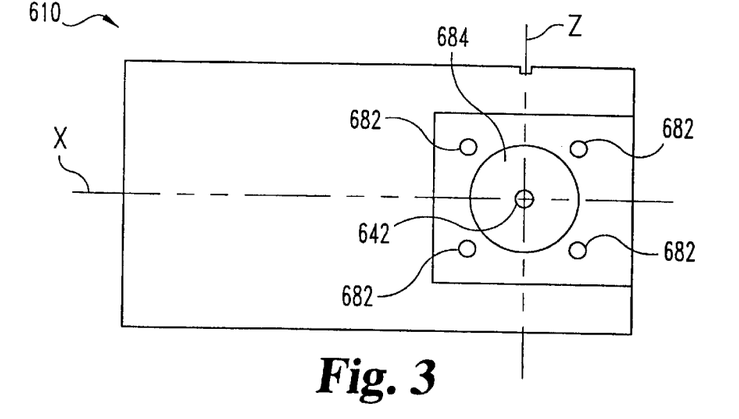
FIG. 3 is a side view of the source block from the FIG. 1 meter.
Figure 4:
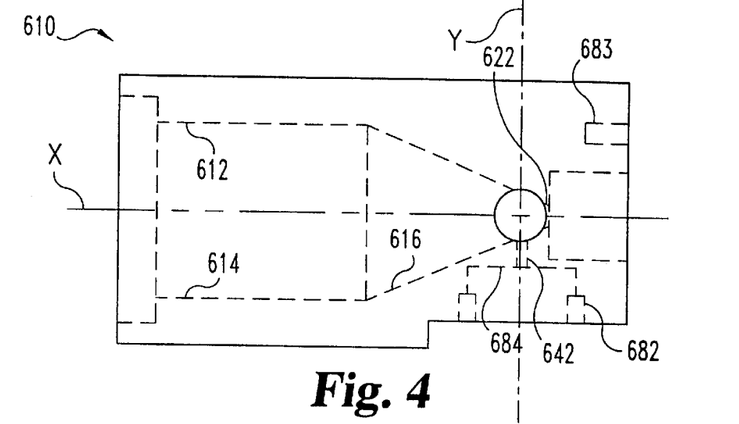
FIG. 4 is a top view of the source block from the FIG. 1 meter.
Figure 5:
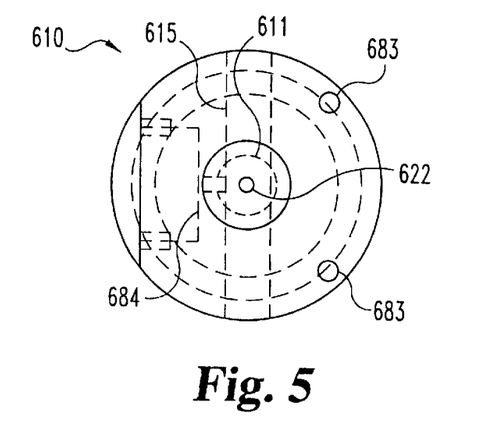
FIG. 5 is an end view of the source block from the FIG. 1 meter.

Turning now to FIGS. 1 and 2, an X-ray fluorescence device 600 is depicted. Device 600 includes a rigid outer stainless steel housing 630 surrounding a plastic source block 610. A pair of fluid couplings 660 are mounted to housing 630 and fluidly connect to a polymer tube 620, which passes through channel 615 of source block 610. A sealed capsule of Cadmium-109 provides an X-ray source 650 contained within source block 610 and a silicon based detector 640 is mounted in seat 680 of source block 610.

"Plastic end piece 618 is friction fit into one end of source block 610 and closes cavity 612 in source block 610. End piece 670 is mounted to the other end of source block 610 and secures X-ray source 650 in block 610. End piece 670 also includes detector mount portion 674 which retains X-ray detector 640 in detector seat 680 of source block 610 and is provided with holes for allowing a signal processing assembly (not shown) electrical access to the pins of detector 640. Mounting holes 682, 683 in source block 610 align with corresponding holes in end piece 670 to facilitate a secure coupling of the end piece 670 and source block 610. End piece 670 includes a lip 676 that fits against the open end 634 of housing 630, and a steel retaining ring 632 is threaded onto housing 630 over end piece 670. End piece 670 is constructed of brass or copper or other material of high thermal conductivity and includes a set of heat conduction fins 672 that extend outside housing 630 to be open to the ambient air."

Fluid coupling assemblies 660 are used to provide rigid fluid connections to tube 620. Assemblies 660 include an outer coupler 662 operable to be coupled to a fluid line. Coupler 662 also has an extension portion 663 which fits inside tube 620. Alignment pin 664 extends through housing 630 to fit into channel 615. Alignment pin 664 has a hollow center to receive extension portion 663 and has an upper flange portion to retain pin 664 outside housing. Pin 664 also serves as a seat for O-ring 668 such that as outer coupler 662 is tightened against pin 664, O-ring 668 compresses against tube 620 to form a fluid tight seal between tube 620 and coupler 662.

Additional X-ray shielding is provided around source 650. Source 650 is contained within a lead X-ray shielding source piece 652. Source 650 is fitted into piece 652 which surrounds source 650 in block 610. Piece 652 has a tapered channel 654 leading to opening 622 in block 610. It is to be understood that piece 652 and block 610 cooperate to effectively shield all source X-rays, save those emanating from source 650 with a trajectory passing through opening 622.

Source block 610 defines a noise reduction cavity 612 positioned opposite source 650 about tube 620 and has opening 611 adjacent tube 620. Cavity 612 is configured to receive those source X-rays with a trajectory passing through opening 622. Both cavity 612 and opening 622 are centered about a common axis, which for purposes of illustration has been designated the x-axis. Cavity 612 includes a conically tapered region 616 adjacent a substantially cylindrical region 614.

Source block 610 also includes aperture opening 642 (see FIGS. 3–6) between detector 640 and tube 620. Opening 642 is centered on the y-axis and is of constant diameter along its length. Tube 620 is centered about the z-axis and, as described below, is substantially transparent to X-rays in the energy ranges of interest.

In one mode of operation, device 600 provides a fluid analysis device for detecting and quantifying selected components of a fluid. In this mode, fluid is passed through tube 620 and metals in the fluid will interact with source X-rays in the suitable energy range (approximately 5–30 KeV) to produce fluorescence X-rays which are then detected by X-ray detector 640. Absorption of a fluorescence X-ray by the X-ray detector 640, for example a silicon based X-ray detector such as the model XR-100CR detector available from AmpTek located in Bedford, Mass., produces an electronic output pulse with an amplitude proportional to the energy of the absorbed X-ray. Signals from the X-ray detector 640 are amplified and shaped and then the individual pulses from individual absorbed X-rays are categorized according to amplitude and recorded with a multichannel analyzer (not shown).

The fluorescence X-ray spectrum can be plotted as X-ray intensity versus energy. The line features of the emitted X-ray spectrum are characteristic for the elemental composition of the sample material and thus are interpreted as fingerprints in elemental identification. With appropriate calibration, line intensities are used in quantitative analyses where background radiation is subtracted by a computer (not shown) used for data processing.

Tube 620 is comprised of low atomic weight elements (e.g., C, H, N) that are relatively transparent to the source X-rays and do not significantly contribute to the fluorescence background signal in the energy bandwidth of interest. Plastic materials, including polymerized carbon materials such as polymides, are candidate materials for the tube 620, though other materials may be used depending on the X-ray source and the particular fluid elements of interest. Tube 620 must also be sturdy enough to withstand normal operating conditions, which when used in on-board machine fluid analysis, such as described in related application Ser. No. 09/776,109 filed Feb. 1, 2001, and titled Apparatus and Method for Fluid Analysis, the disclosure of which is hereby incorporated by reference, might include machine vibrations and elevated fluid temperatures and pressures. Other applications of device 600 include those described in U.S. Pat. No. 5,982,847 to Nelson, the disclosure of which is also hereby incorporated by reference.

As a general rule, the more transparent tube 620 is to X-rays of interest, the better the system performance. Tube 620 can be made sufficiently transparent to source and fluorescent X-rays by being thin walled. The exact thickness of the tube walls effective to achieve the desired degree of X-ray transmission depends at least to some extent, on several factors. Among these factors are the composition of the tube, the type and proximity of the X-ray source to tube 620, the desired flux of X-rays through the fluid, and the type and concentration of element to be detected in the fluid. For a detection of iron in lubricating engine oil, a polymide tube having walls 0.003 inches thick has been found to be effective. While structural rigidity would likely provide a lower limit to the wall thickness, polimide tubes with wall thickness below about 0.005 inches would be satisfactory.

It is to be understood that X-rays from the source strike fluid in the tube to provide the fluorescent X-rays of interest, but the fluid in the tube also produces noise in the form of X-rays not associated with the fluorescing elements of interest. By sizing the tube to be consistent with the absorption length for an X-ray of interest, the signal-to-noise ratio can be reduced. For example, for calcium fluorescence X-rays in a carbon-based fluid of density about 1 g/cm3, the adsorption length is about 0.009 inch while for zinc fluorescence X-rays the length is about 0.138 inch. When assaying for a wide variety of elements, one preferable approach is to match the sample dimension to the adsorption length of some element near the center of the analytical range. A preferred range for the inside diameter of tube 620 is between about 0.05 and about 0.25 inches. In the illustrated embodiment, tube 620 is about 0.12 inch inside diameter.

In the illustrated embodiment of device 600, a low atomic number fluid, such as water or carbon based fluids, could be expected to adsorb about 10% of the X-rays emanating from the cadmium-109 source 650. The remainder of the source X-rays are transmitted and strike the source block walls forming cavity 612. There is nothing but air in the vicinity of tube 620, and thus noise attributable to scattering of the beam of source X-rays is minimized.

In addition to being spatially removed from detector aperture 642, the walls of cavity 612 are formed of a low atomic number material which serves to further reduce noise. In the illustrated embodiment, block 610 is a plastic such as nylon, Ultem, PEEK, teflon, Delrin, carbon tetra fluoride, or tetra fluoroethylene (TFE), which advantageously are each highly machineable and contain no elements of higher atomic number than fluorine. Other candidate materials for source block 610 include magnesium, carbon (graphite), aluminum, silicon and alloys thereof or other similar materials of low atomic number. Fluorescence X-rays from these exemplary low atomic number materials would typically be of too low an energy to substantially contribute to noise over the energy range of interest. In addition, the probability of low atomic number elements producing X-rays, either by Compton or Thomson scattering is lower than higher atomic number elements on a per atom basis.

In one preferred embodiment, a major portion of source block 610 is formed of a material having elements with an atomic number below the atomic number of the element of lowest atomic number of interest in the fluid. For many applications, the atomic number of the source block material is below 15. While in the illustrated embodiment, source block 610 is formed of a single piece of material, a layered approach is also contemplated where the outer portion of block 610 is formed of a higher atomic number material, such as lead or tungsten, with interior surfaces of block 610 (such as cavity 612, channel 615, and/or opening 622) lined with lower atomic number materials.

While source block 610 provides one level of X-ray shielding, depending on its wall thickness and the relative strength of the source X-rays, block 610 may not fully contain all source X-rays. Additional X-ray shielding is thus optionally provided around block 610. A thin layer 692 of lead approximately 0.12 inches thick surrounds source block to assure that no X-rays escape device 600. A thin layer 690 of tin about 0.007 inches thick is wrapped around block 610 inside of the lead layer 692 and serves to capture any fluorescence X-rays from the lead layer 692 from being re-radiated back into block 610.

Additional shielding foils 686 and 688 are also provided between detector 640 and block 610. Gold foil 686 is positioned in seat 680 abutting face 684 (See FIGS. 3–5) followed by indium foil 688 and then detector 640. Foils 686 and 688 are each about 0.03 inches thick and each include holes 0.04 inch holes that align with source block aperture 642 which is approximately the same size (see FIG. 4). Foils 686 and 688 are chosen to have a high atomic number and do not produce a signal that interferes with the analysis of the elements of interest. Detector 640 preferably has a detection face parallel to surface 684 that is sized to receive all the fluorescence X-rays coming through aperture 642. Most preferably, the detection face is larger than necessary such that fluorescence X-rays strike the center portion of the detector 640 and avoids striking the detector edges.

In the illustrated embodiment, no X-ray collimating or focusing equipment is provided in device 600 either between source 650 and tube 620 or between tube 620 and detector 640. Considering both source 650 and the excited fluid in tube 620 as point sources of X-rays, the X-ray flux density decreases exponentially with increasing distance between tube 620 and either detector 640 or source 650. Preferably therefore, in the absence of collimating or focusing equipment, source 650 and detector 640 are placed in close proximity to tube 620 so as to deliver and receive X-rays of a desired high X-ray flux density through openings 622 and 642 respectively. It is to be understood that, in this configuration, while source 650 and detector 640 are also in close proximity, they are isolated from each other by source block 610, and thus detector noise attributable to the proximity of source 650 can be reduced. While in the illustrated embodiment no collimating or focusing equipment is provided, such equipment could optionally be incorporated into device 600, though it is expected that such a modification would add to the size of device 600 and/or add additional cost to its manufacture.

It is contemplated that device 600 can be used for fluid analysis for a wide range of elements. For analysis that focuses on lower atomic number elements, such as silicon, sulfur, aluminum, or phosphorous, it is expected that a smaller tube diameter might be utilized, for example in the range of 0.01 to 0.03 inch inside diameter. Alternatively or in addition, analysis for lower atomic number element could utilize a lower energy X-ray source, such as for example iron-55, which might eliminate any need for additional X-ray shielding beyond that provided by block 610. One particular application for a lower energy source is the monitoring of jet engines which typically include silicon in some of the parts. Alternatively, combustion of air which includes silicon (in the form of dirt and dust) can be monitored by analysis for silicon in oil. As described above, when monitoring for the presence of silicon in a fluid, source block 610 is advantageously formed of material with an atomic number below 14, the atomic number of silicon.

Figure 6:
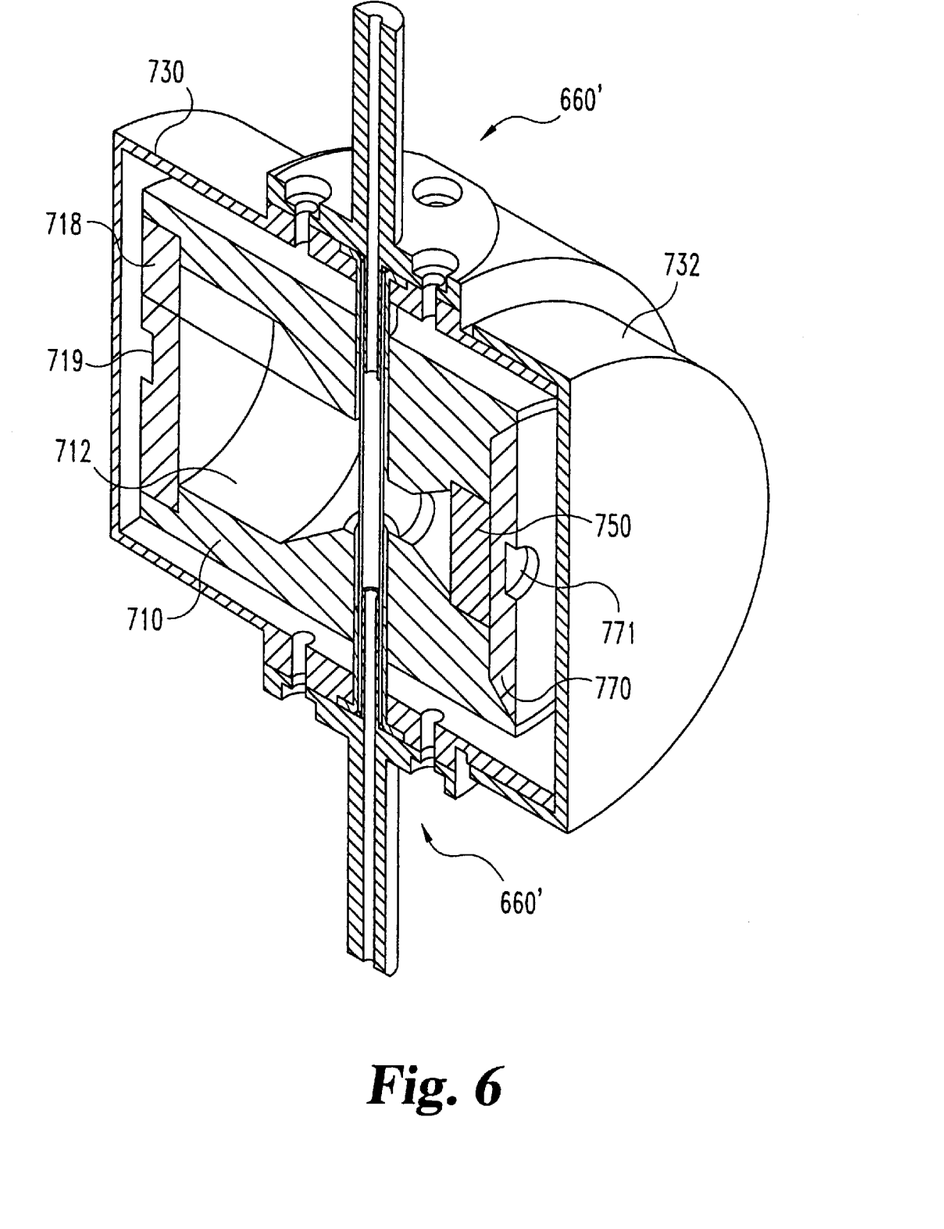
FIG. 6 is a perspective sectional view of another x-ray fluorescence meter.
Figure 7:
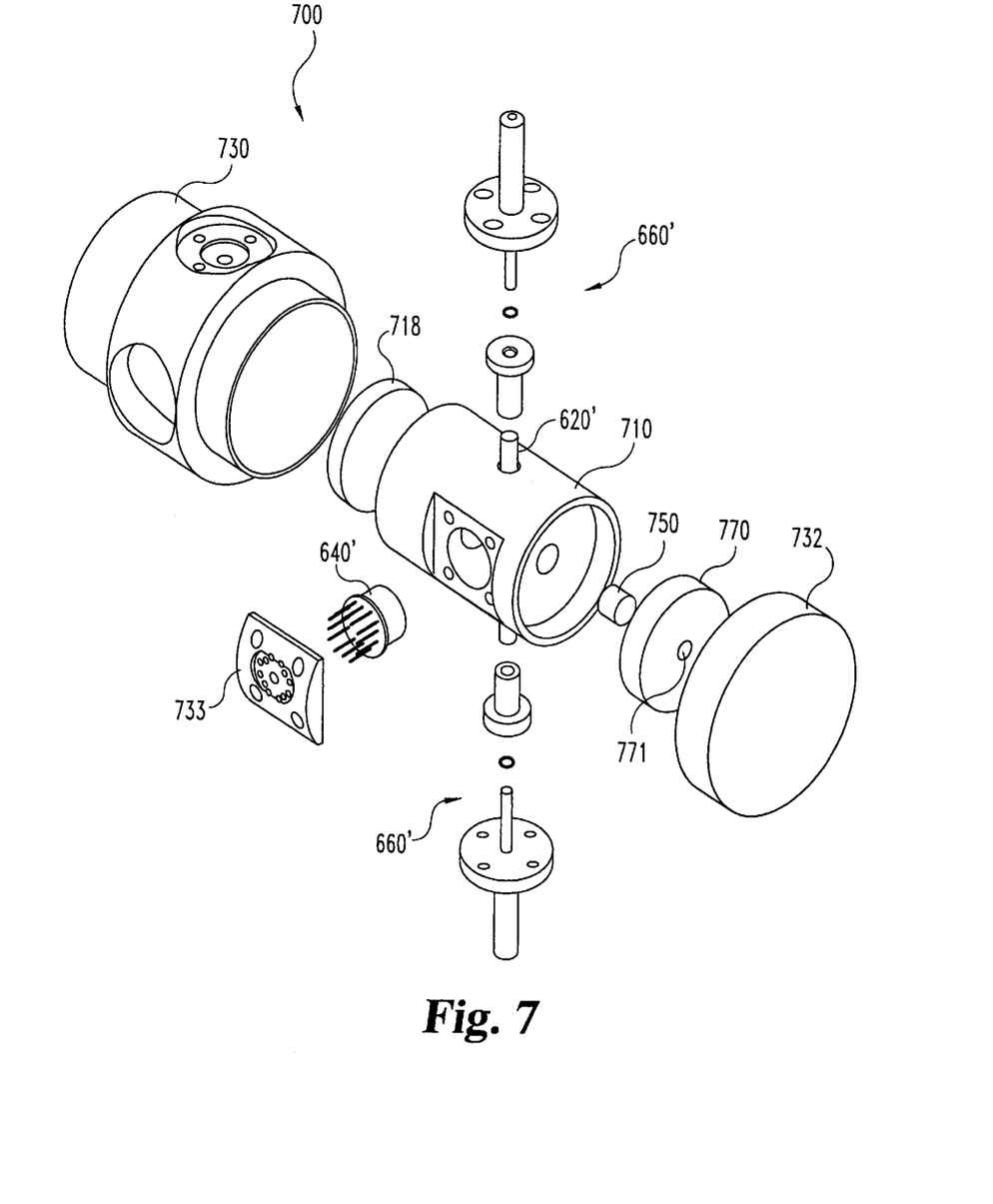
FIG. 7 is an assembly view of the FIG. 6 x-ray fluorescence meter.
Figure 8:
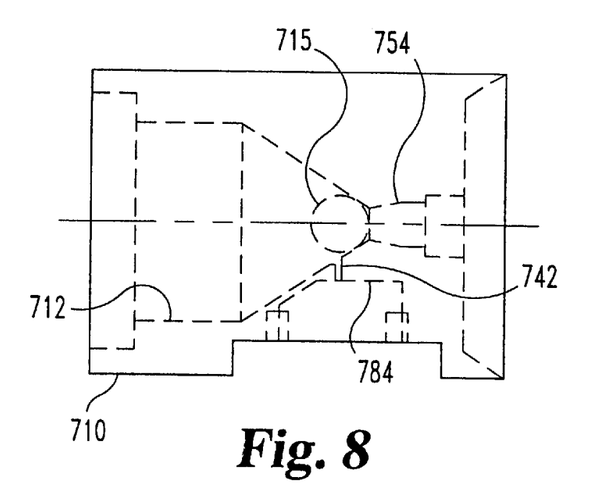
FIG. 8 is a top view of the source block from the FIG. 6 meter.

Turning now to FIGS. 6–8, another fluid analysis device 700 is depicted. Device 700 includes an outer steel housing 730, 232 surrounding a magnesium source block 710. A sealed X-ray source 750 is contained in source block 710 adjacent passage 754 in block 710. Source 750 is closed in block 710 by end cap 770, and end cap 770 includes a recess 771 that can be filled with additional X-ray shielding material such as lead or the like. End cap 718 closes cavity 712 of source block 710 and end cap 718 also includes a recess 719 for receiving additional X-ray shielding material."

A pair of fluid couplings 660' connect to polyimide tube 620'. Couplings 660' are mounted to housing 730 and align with channel 715 in the manner described above with respect to device 600. Detector 640' is received in source block 710 and retained therein by brass piece 733 that fits over the pins of detector 640' and mounts to block 710 with a set of screws through the provided holes in block 710. The detector face abuts face 784 in block 710 and detector 740 is operable to receive the X-ray fluorescence response from fluid in tube 620' that passes through opening 742 in block 710. Device 700 also includes additional X-ray shielding (not shown) around block 710 and between detector 640' and block 710 as described with respect to device 600.

In both device 600 and device 700, source X-rays travelling through the flow path are centered about the X-axis and detectors 640, 640' are aligned along the Y axis. It is also contemplated that the sources 650, 750 and detectors 640, 640' could be aligned along non-orthogonal axes and/or non-intersecting axes. In one variation, the sources 650, 750 and detectors 640, 640' are aligned along axes intersecting at an angle of between 75 and 115 degrees. In addition, while the flow path through the devices 600, 700 is aligned along the Z-axis, it is also contemplated that it could be oriented aligned along an axis non-orthogonal and/or non-intersecting with either the detector axis (Y-axis) or the source axis (X-axis). For example, in one variation the detector axis intersects near a wall, rather than in the center of, the flow path so as to increase detection of fluorescing elements having a lower X-ray absorption length.

Figure 9:
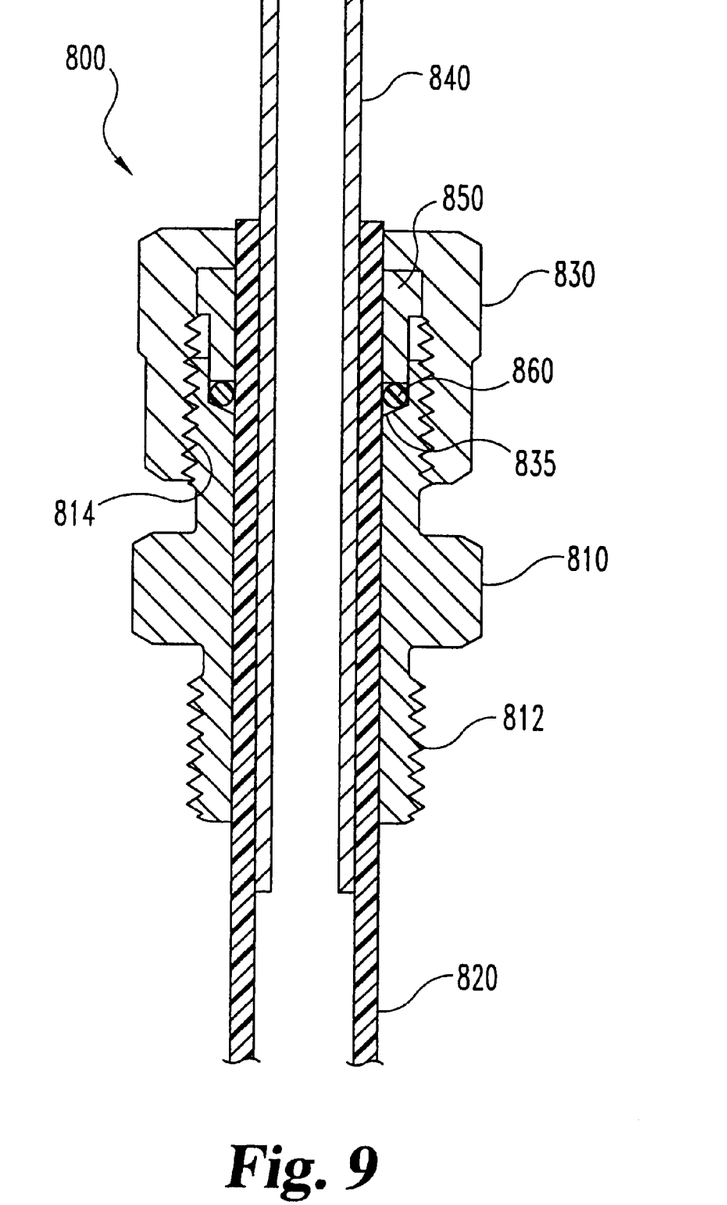
FIG. 9 is a sectional view of a fluid coupling assembly.

"Turning now to FIG. 9, an exemplary fluid coupling assembly 800 is depicted. Assembly 800 is used to couple a metal machine fluid line 840, such as stainless steel tubing, to a piece of relatively soft plastic tubing 820 in a machine fluid analysis device according to the present invention. Assembly 800 includes piece 810 having a first set of threads 812 for connection to an outer housing. Piece 810 has a central lumen that receives the soft tubing 820 with the rigid tubing 840 being received inside tubing 820. Piece 830 fits around piece 810 and threadedly engages a second set of threads 814 on piece 810. When piece 830 is screwed onto piece 810 it compresses piece 850 against O-ring 860 which also abuts angled surface 835 of piece 810 and is thereby compressed against tube 820 to form a fluid tight seal."

Figure 10:
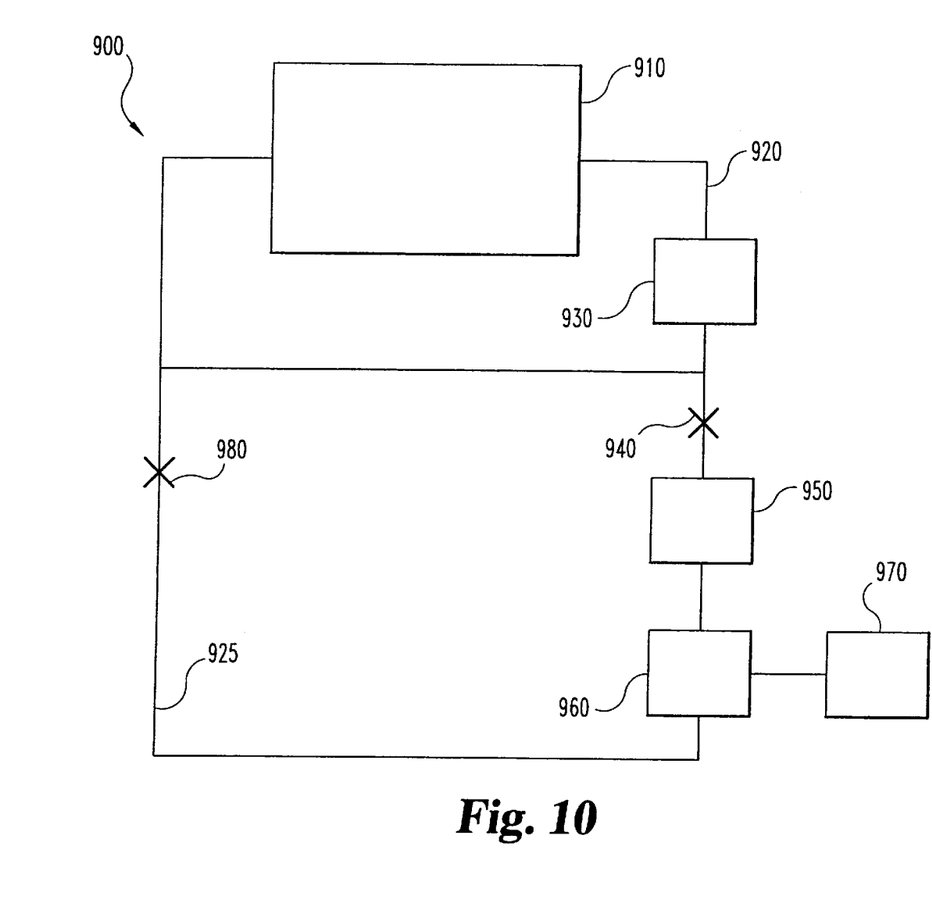
FIG. 10 is a schematic illustration of a system utilizing an x-ray fluorescence meter according to a further embodiment of the present invention.

Turning now to FIG. 10 a system 900 for monitoring a lubricating oil from a machine is depicted. System 900 includes a machine 910 having an oil line 920 and an oil pump 930. A second oil line 925 is separated from the main line 920 by a master valve 940. When master valve 940 is open, a portion of the oil in line 920 passes through a second line 925. An oil cooler 950 and an X-ray fluorescence meter 960 are provided in series on second line 925. Oil exiting meter 960 then passes through a one way valve 980 before re-joining oil in the main line 920 where it is circulated back through the machine 910 under action of pump 930.

A computer 970 receives signals from meter 960 and includes signal processing electronics and programming instructions operable to determine the presence and amount of wear metal particles in the lubricating oil in line 925 based on the signals received from the X-ray detector of meter 960. The computer 970 can be assembled from commercially available components and programmed to perform the tasks related to X-ray fluorescence spectroscopy according to the present invention. Alternatively, special purpose computers designed specifically to accomplish one or more tasks can also be used. Tasks to be performed by computer 970 include collecting fluorescent X-ray intensity data, subtracting background data, and converting fluorescent X-ray data into part per million concentration values. The computer and accompanying programs are one embodiment of a structure capable of processing the signal from the X-ray fluorescence meter 960 in order to determine the presence and amount of wear metal particles in the lubricating oil in line 925. Alternatively or in addition, computer 970 in combination with multi-channel detector 640 form a detector assembly operable to quantitatively determine fluorescent photon counts for photons having different energy levels. The detector assembly includes programming instructions operable to fit signature fluorescence spectra from known elements to the determined fluorescent photon counts to thereby determine the presence of multiple elements in a single sample.

Computer 970 also outputs the determined concentration data to a system operator or controller. In one preferred embodiment, the concentration values are transmitted to a remote observer of engine health in the manner described in U.S. application Ser. No. 09/776,109 filed Feb. 1, 2001, and assigned to the same assignee of the present invention.

In the illustrated embodiment, meter 960 is provided on a separate oil line 925 from the main oil line 920 and thus meter 960 interrogates oil selectively diverted from the main line. It is also contemplated that meter 960 can be provided on oil line 920 and thus be operable to interrogate all oil passing through line 920, rather than oil selectively diverted therefrom.

It is understood that while the primary focus of the description above relates to machine fluids, the present invention should not be so limited. As is apparent to those skilled in the art, such an X-ray fluorescence apparatus and method have applications beyond that of machine fluids to any flowing, or intermittently-flowing, fluids. As one example, the techniques described herein would be useful to analyze concentrations of constituents in a fluid process line at an industrial facility, for example measuring suspended metals or soaps in a process line.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. All publications, patents, and patent applications cited in this specification are herein incorporated by reference as if each were specifically and individually indicated to be incorporated by reference and set forth in its entirety herein.

What is claimed is:

1. A method of monitoring a fluid comprising:
    providing an X-ray fluorescence meter including;
        a source block containing an X-ray source,
        a rigid outer housing surrounding the source block,
        a fluid flow path through the housing and the source block and past the X-ray source, and
        a detector proximate the flow path and isolated from source X-rays by the source block,
        wherein the source block defines a noise reduction cavity having an opening thereto adjacent the flow path and opposite the X-ray source such that the flow path is between the noise reduction cavity and the X-ray source,
    passing fluid through the flow path,
    passing X-rays from the X-ray source through the flow path and into the noise reduction cavity, and
    with the detector, receiving a fluorescence response from fluid in the flow path interacting with the X-rays.

2. The method of claim 1 wherein the housing includes a pair of fluid couplings in communication with a passage substantially transparent to source X-rays forming a portion of the flow path, the method further comprising:
    coupling a machine fluid line to the fluid couplings to provide a machine fluid flow path through the source block, and
    passing machine fluid through the flow path.

3. The method of claim 2 wherein the machine fluid is passed through the source block under pressure of the machine.

4. The method of claim 3 further comprising:
    mounting the housing to a machine wherein the machine fluid is from the machine,
    performing machine fluid analysis while operating the machine.

5. The method of claim 3 wherein the flow path is provided by a thin-walled passage of low element weight composition.

6. The method of claim 2 further comprising:
    aligning the source block in the housing with a pair of alignment pins contacting the housing and the source block, the alignment pins forming a portion of the pair of fluid couplings.

7. The method of claim 1 wherein a substantial portion of the source block includes material selected from the group consisting of aluminum, magnesium, graphite, and plastic.

8. The method of claim 1 wherein the presence of a selected element in the fluid is detected and wherein a substantial portion of source block includes material having an atomic number less than the atomic number of the selected element.

9. The method of claim 1 wherein the X-ray source is shielded in the source block such that there is no path for substantial amounts of source X-rays to freely travel except in an unshielded direction toward the flow path.

10. The method of claim 8 wherein the detector is mounted to the source block and shielded from the X-ray source and the cavity by the source block and wherein an aperture is provided in the source block between the flow path and the detector such that substantially only X-rays emanating from the fluid in the flow path can directly reach the detector.

11. An X-ray fluorescence meter comprising:
    a source block containing an X-ray source,
    a fluid flow path through the source block and proximate the X-ray source,
    wherein the flow path is substantially transparent to source X-rays and operable to direct a fluid past the X-ray source for interaction of the fluid with source X-rays to produce a fluid fluorescence response to the source X-rays,
        a detector mounted in the source block proximate the flow path and separated from the X-ray source by the source block, the detector being operable to receive at least a portion of the fluorescence response, and
        a rigid outer housing surrounding the source block and including a pair of fluid couplings connected to the flow path,
    wherein the source block defines a noise reduction cavity separated from the detector by the source block and operable to receive source X-rays passing through the flow path, the noise reduction cavity having an opening thereto adjacent the flow path and opposite the X-ray source such that the flow path is between the cavity opening and the X-ray source.

12. The meter of claim 11 wherein the flow path defines a bulk fluid flow direction for fluid in the flow path and the detector has a detection face in a plane substantially parallel to the flow direction.

13. The meter of claim 11 wherein the flow path defines a bulk fluid flow direction for fluid proximate the X-ray source and the approximate center of the detector, the approximate center of the X-ray source, and the approximate center of the flow path proximate the detector define a plane substantially non-parallel to the flow direction.

14. The meter of claim 13 wherein the approximate center of the detector, the approximate center of the X-ray source, and the approximate center of the flow path proximate the X-ray source define a plane substantially perpendicular to the flow direction.

15. The method of claim 11 wherein a substantial portion of the source block includes material selected from the group consisting of aluminum, magnesium, graphite, and plastic.

16. The method of claim 11 wherein a substantial portion of source block includes material having an atomic number less than 15.

17. The meter of claim 11 wherein the flow path is provided by a thin-walled passage of low element weight composition.

18. The meter of claim 17 wherein the thin-walled passage is a tube.

19. The meter of claim 11 wherein the noise reduction cavity has a closed end and includes a substantially cylindrical portion and a substantially tapered region tapered towards the cavity opening.

20. The meter of claim 11 wherein the source block includes an X-ray source chamber and a source aperture is provided between the X-ray source chamber and the flow path such that substantially only the source X-rays passing through the source aperture can interact with fluid in the flow path, wherein the source aperture is constructed of a material different from the material forming a substantial portion of the source block.

21. The meter of claim 20 wherein the source aperture is provided by a substantially continuously tapered passage.

22. The meter of claim 20 wherein the source aperture includes lead.

23. The meter of claim 11 wherein a detector aperture is provided in the source block between the flow path and the detector such that substantially only X-rays emanating from the fluid in the flow path can directly reach the detector.

24. The meter of claim 23 wherein at least one layer of X-ray shielding material is provided between the detector and the source block, the X-ray shielding material having an opening therein aligned with the detector aperture in the source block.

25. The meter of claim 11 wherein each of the fluid couplings include an alignment pin in contact with an opening in the housing and an opening in the source block to thereby provide relative support between the housing and the source block.

26. The meter of claim 11 further comprising:
an end piece securing the X-ray source in the source block, the end piece being secured to the housing.

27. The meter of claim 26 wherein the end piece has at least one hole for receiving a portion of the detector.

28. The meter of claim 27 wherein the end piece includes at least one heat conduction fin outside the housing.

29. The meter of claim 11 wherein the source block is not in contact with the housing around a substantial portion of the source block.

30. The meter of claim 11 wherein the housing includes a mounting bracket for coupling the device to a machine to provide an on-board machine fluid analysis device.

31. The meter of claim 11 wherein the detector is a multi-channel detector and the detector is coupled to a processor to form a detector assembly operable to quantitatively determine fluorescent photon counts for photons having different energy levels to thereby determine the presence of multiple elements in a single sample.

32. The meter of claim 11 wherein the X-ray source is a sealed isotopic X-ray source.

33. The meter of claim 11 wherein the X-ray source produces X-rays having energy level between about 5 KeV and about 30 KeV.

34. The meter of claim 11 further comprising at least one layer of X-ray shielding material between at least a portion of the source block and the housing.

35. The meter of claim 34 wherein the at least one layer of shielding material includes two layers of different material compositions.

36. The meter of claim 11 wherein the flow path has a width proximate the X-ray source between about 0.050 inches and about 0.250 inches.

37. The meter of claim 11 wherein the flow path has a width proximate the X-ray source less than about 0.200 inches.

38. A method comprising:
placing a meter according to claim 11 proximate a machine and in fluid communication with a machine fluid such that the machine fluid passes through the flow path under pressure of the machine,
monitoring the machine fluid with the device.

39. The meter of claim 11 wherein there is no X-ray collimating or focusing assembly between the X-ray source and the flow path.

40. An X-ray fluorescence meter for monitoring a machine fluid comprising:
an X-ray source,
a source block containing the X-ray source and having a flow path therethrough substantially transparent to source X-rays and defining a bulk fluid flow direction through the source block,
a first opening in the source block between the flow path and the X-ray source wherein at least a portion of the source X-rays travel through the opening and the flow path in a direction substantially perpendicular to the fluid flow direction,
an X-ray detector substantially isolated from source X-rays by the source block,
a second opening in the source block between the flow path and the detector
wherein the detector is operable to receive at least a portion of a fluorescence response of a fluid in the flow path interacting with source X-rays passing through the flow path,
a pair of fluid couplings operable to connect the flow path to a machine fluid line to form a machine fluid flow path through the source block.

41. The meter of claim 40 wherein the source block defines a noise reduction cavity to reduce detector noise attributable to source X-ray interaction with the source block, the noise reduction cavity having an opening thereto adjacent the flow path and opposite the X-ray source such that the flow path is between the noise reduction cavity and the X-ray source.

42. The meter of claim 41 wherein there is no X-ray collimating or focusing assembly between the X-ray source and the flow path.

43. The meter of claim 40 wherein the detector has a detection face defining a plane substantially parallel to the bulk fluid flow direction.

44. The meter of claim 43 wherein the flow path is provided by a thin walled passage of low element weight composition.

45. The meter of claim 40 further comprising a rigid outer housing surrounding the source block wherein at least one layer of X-ray shielding material is between at least a portion of the source block and the housing.

46. The meter of claim 45 wherein the at least one layer is two layers of different material composition.

47. The meter of claim 40 further comprising at least one layer of X-ray shielding material between the detector and the source block.

48. The meter of claim 40 wherein the fluid couplings include a pair of alignment pins in contact with a rigid outer housing surrounding the source block and an opening in the source block.

49. The meter of claim 40 wherein the source block comprises plastic.

50. The meter of claim 49 wherein the X-ray source provides X-rays in an energy range from about 5 KeV to about 30 KeV.

51. The meter of claim 40 wherein at least an interior surface of the source block is provided by a material having elements with atomic number below 15.

52. An X-ray fluorescence meter comprising:

an X-ray shielding source block containing an X-ray source, wherein a substantial portion of the source block includes material having elements with an atomic number less than 15, a fluid flow path through the source block and proximate the X-ray source, wherein the fluid flow path is substantially transparent to source X-rays, and a fluorescence X-ray detector mounted to the source block proximate the flow path and separated from the X-ray source by the source block, a first opening in the source block between the X-ray source and the flow path for passage of source X-rays through the flow path, a second opening in the source block between the flow path and the detector for passage of fluid fluorescence response from a fluid in the flow path interacting with source X-rays, and a noise reduction cavity in the source block and having an opening thereto adjacent the flow path and opposite the X-ray source for receiving source X-rays that pass through the flow path.

53. The meter of claim 52 wherein the X-ray source produces X-rays having energies between about 5 KeV and about 30 KeV.

54. The meter of claim 52 further comprising a piece of X-ray shielding material between the X-ray source and the first opening in the source block.

55. The meter of claim 54 wherein the piece of X-ray shielding material surrounds the X-ray source and has an opening aligned with the first opening.

56. The meter of claim 54 wherein there is no X-ray collimating or focusing assembly between the X-ray source and the flow path.

57. The meter of claim 52 further comprising at least one piece of X-ray shielding material between the detector and the source block and having a hole therein aligned with the second opening.

58. The meter of claim 52 further comprising a rigid outer housing surrounding the source block, and a pair of fluid couplings mounted to the outer housing and connected to the flow path.

59. The meter of claim 58 wherein the fluid couplings include an alignment pin in contact with the housing and an opening in the source block.

60. The meter of claim 52 wherein a major portion of the source block is material selected from the group consisting of aluminum, magnesium, graphite, and plastic.

61. A method comprising:

providing a meter according to claim 52, passing fluid through the flow path.

\* \* \* \* \*